United States Patent
Narula et al.

(10) Patent No.: US 6,924,263 B2
(45) Date of Patent: Aug. 2, 2005

(54) OXIME METHYL ETHERS

(75) Inventors: Anubhav P. S. Narula, Hazlet, NJ (US); Rajamony Mahesh, Chennai (IN); Manfred Pawlak, Princeton, NJ (US); Clint Dee Winton Brooks, Sea Bright, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 377 days.

(21) Appl. No.: 10/232,200

(22) Filed: Aug. 29, 2002

(65) Prior Publication Data

US 2004/0043917 A1 Mar. 4, 2004

(51) Int. Cl.$^7$ .................................................. A61K 7/46
(52) U.S. Cl. .............................. 512/25; 512/8; 512/11; 512/12; 512/20; 568/579; 568/583; 568/626; 510/101
(58) Field of Search .................................. 512/8, 11, 12, 512/20, 25; 368/579, 583, 626; 510/101

(56) References Cited

U.S. PATENT DOCUMENTS

| | | | |
|---|---|---|---|
| 4,388,464 A | * | 6/1983 | Kristinsson et al. ........ 548/136 |
| 4,534,891 A | | 8/1985 | Boden et al. |
| 4,985,402 A | | 1/1991 | Narula et al. |
| 5,143,899 A | | 9/1992 | Narula et al. |
| 5,179,222 A | | 1/1993 | Narula et al. |
| 5,236,897 A | | 8/1993 | Narula et al. |
| 5,300,488 A | | 4/1994 | Narula et al. |
| 5,321,144 A | * | 6/1994 | Narula et al. ................ 549/442 |

FOREIGN PATENT DOCUMENTS

EP    0 672 746 A1    9/1995

OTHER PUBLICATIONS

U.S. Appl. No. 10/231,690, filed Aug. 29, 2002, Narula et al.
Chowdhury, et al, Synthesis and Insect Growth Regulatory Activity of Alkoxy–Substituted Benzaldoxime Ethers, J.Agric.Food Chem. 1988, 46–731–736.
Walia, et al, Synthesis and Synergistic Activity of Oxime Ethers Containing A Benzo–1,3–Dioxole Group, J.Agric-.Food Chem. 1985, 33, 308–310.

* cited by examiner

*Primary Examiner*—Monique T. Cole
(74) *Attorney, Agent, or Firm*—Joseph F. Leightner, Esq.

(57) ABSTRACT

The use of various oxime ethers are described as fragrance chemicals, suitable for use in creating fragrance, and scents in items such as perfumes, colognes and personal care products is disclosed. Novel compounds are also disclosed.

16 Claims, No Drawings

OXIME METHYL ETHERS

FIELD OF THE INVENTION

The use of oxime methyl ethers is disclosed as fragrance chemicals suitable for incorporation in fine fragrances, cosmetics, toiletries and related applications.

BACKGROUND OF THE INVENTION

There is an ongoing need in the fragrance industry to provide new chemicals to give perfumers and other persons ability to create new fragrances for perfumes, colognes and personal care products.

One class of compounds that have been found to be particularly useful as fragrance chemicals are oxime ethers, more specifically propionitrile and propiohydroxyamine derivatives described in U.S. Pat. Nos. 4,985,402; 5,143,899; 5,179,222; 5,236,897, 5,300,488; and 5,321,144; the contents hereby incorporated by reference as if set forth in its entirety; and European Patent Application 672,746.

Despite these disclosures there is an ongoing need to provide new fragrance chemicals in order to allow perfumers to create new fragrances and scents.

SUMMARY OF THE INVENTION

The present invention is directed to novel compounds selected from the group of Formula A set forth below:

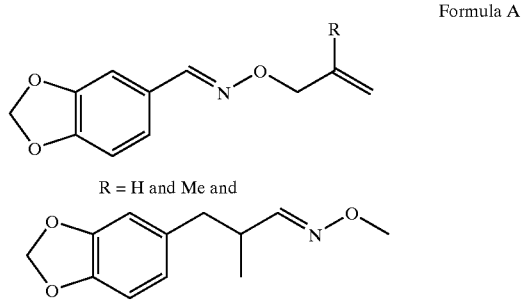

R = H and Me and

The present invention is directed to the use of the above oxime ethers as fragrance chemicals to enhance fragrance in perfumes, toilet waters, colognes, personal products and the like. In addition, the present invention also includes a method for enhancing a perfume by incorporating an olfactory acceptable amount of compounds set forth above as well the additional compounds of Formula B set forth below:

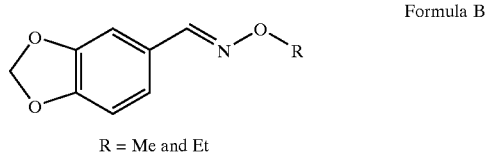

R = Me and Et

These and other embodiments of the present invention will be apparent by reading the following specification.

DETAILED DESCRIPTION OF THE INVENTION

The present invention is directed to the use of the compound, oxime ethers in fragrance formulations. The compounds of Formula B have been disclosed in the art and their preparation of compounds is known in the art, *Synthesis and insect growth regulatory activity of alkoxy-substituted bezaldoxime ethers*, The Journal Agricultural Food Chemistry, (1998) 46(2), p 731–736 which discloses the use of oxime ethers as pesticides.

Those with skill in the art will appreciate that in Formula B, above when R is methyl the compound is 1,3-benzodioxole-5-carboxaldehye, O-methyloxamine; when R is ethyl the compound is 1,3-benzodioxole-5-carboxaldehye, O-ethyloxamine; in Formula A when R is allyl the compound is 1,3-benzodioxole-5-carboxaldehye, O-allyloxamine; and when R is methylallyl the compound is 1,3-benzodioxole-5-carboxaldehye, O-methallyl-oxamine.

These compounds can be prepared by the following general reaction sequence. An appropriate size reaction flask equipped with a mechanical stirrer, condenser, addition funnel, and a temperature measurement thermocouple, is first charged with a given aldehyde and a suitable solvent such as ethylbenzene, toluene, and xylene at room temprature. To this is added an aqueous solution of hydroxylamine sulphate followed by a slow addition of 50% aqueous sodium hydroxide until basic and while maintaining the temperature below 40 degrees. The mixture is aged for 1 hour. The reaction mass is washed with brine (10% aqueous solution), which gives an oxime that is distilled before use. These oximes were converted to oxime ethers using sodium hydride and appropriate alkylating agent, see the following experimental text for more specific examples.

We have discovered that the above described oxime ethers have a floral fruity note, with slightly green, sweet notes that are well suited for use as a fragrance chemical.

The use of this compound is widely applicable in current perfumery products, including the preparation of perfumes and colognes, the perfuming of personal care products such as soaps, shower gels, and hair care products as well as air fresheners, candles and cosmetic products. The compound can also be used to perfume candles and cleaning agents, such as, but not limited to soaps, detergents, dishwashing materials, scrubbing compositions, window cleaners, and the like.

In these preparations, the compound of the present invention can be used alone or in combination with other fragrance compositions, solvents, adjuvants and the like. Those like. Those with skill in the art will appreciate the nature and variety of the other ingredients that can be used in combination with the compound of the present invention.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk; flower scents such as lavender-like, rose-like, iris-like, and carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

As used herein olfactory effective amount is understood to mean the amount of compound in perfume compositions the individual component will contribute to its particular olfactory characteristics, but the olfactory effect of the perfume composition will be the sum of the effects of each of the perfume or fragrance ingredients. Thus the compounds of the invention can be used to alter the aroma characteristics of the perfume composition by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.1 to about 8 and most preferably from about 0.5 to about 5 weight percent. In addition to the compounds, other agents can be used in conjunction with the fragrance. Well known materials such as surfactants, emulsifiers, and polymers to encapsulate the fragrance can also be employed without departing from the scope of the present invention.

Another method of reporting the level of the compound of the invention in the perfumed composition, i.e., the compounds as a weight percentage of the materials added to impart the desired fragrance. The compounds of the invention can range widely from 0.005 to about 10 weight percent of the perfumed composition, and preferably from about 0.1 to about 5 weight percent. Those with skill in the art will be able to employ the desired level of the compound of the invention to provide the desired fragrance and intensity.

The following are provided as specific embodiments of the present invention. Other modifications of this invention will be readily apparent to those skilled in the art, without departing from the scope of this invention. As used herein all percentages are weight percent. IFF as used in the examples is understood to mean International Flavors & Fragrances Inc., DPG is understood to mean dipropylene glycol, DEP is understood to mean diethylphthalate. As used in this specification Me is understood mean a methyl group, Et is understood to mean an ethyl group and H is understood to be hydrogen.

EXAMPLE 1

Preparation of (1E)-2-(2H-benzo [3,4-D] 1,3-dioxolan-5-yl)-1-aza-1-methoxyethene To a dry 2 liter multi-neck round bottom flask fitted with an air stirrer, nitrogen inlet condenser and an addition funnel, 36 grams of NaH (supplied by Fluka as a 60% dispersion in oil) was added. The flask was maintained at a constant temperature of 20° C. via a water bath. The NaH was washed with three 30 milliliter doses of petroleum ether and the washings were discarded. Tetrahydrofuran (THF) was added to the flask (350 ml), followed by 130 grams of heliotropine oxime in 300 ml of THF over a two hour period while being vigorously stirred. After the addition was complete, 142 grams of methyl iodide in 250 ml of THF was slowly added over two hours. The resulting mixture was stirred at room temperature for twenty-hour hours until the oxime was consumed.

The viscous mass was cooled to 10° C. and then 25 ml of water was added under vigorous stirring. The resulting mass was transferred to a 5 liter separatory funnel. 500 ml of solvent ether is added to the reaction product and the organics were washed with three 250 ml of water until the aqueous layer was pH neutral. The organic layer was dried over sodium sulfate and the solvent was removed under reduced pressure to provide 125 grams of the crude product. The crude product was cooled in ice to give a white solid.

NMR data 3.9 ppm (s, 3H), 6 ppm (s, 2H), 6.7–7.3 ppm (m, 4H), 8 ppm (s, 1H).

The fragrance of this compound was evaluated and was described as methyl chavicol, coumarin, cherry blossom, ozony, and vanillin.

EXAMPLE 2

Preparation of (1E)-2-(2H-benzo [3,4-D] 1,3-dioxolan-5-yl-1-aza-1-ethoxyethene

To a dry 2 liter multi-neck round bottom flask fitted with an air stirrer, nitrogen inlet condenser and an addition funnel, 41 grams of NaH (supplied by Fluka as a 60% dispersion in oil) was added. The flask was maintained at a constant temperature of 20° C. via a water bath. The NaH was washed with three 35 milliliter doses of petroleum ether and the washings were discarded. Tetrahydrofuran (THF) was added to the flask (350 ml), followed by 150 grams of heliotropine oxime in 350 ml of THF over a two hour period while being vigorously stirred. After the addition was complete, 160 grams of ethyl iodide in 300 ml of THF was slowly added over two hours. The resulting mixture was stirred at room temperature for 40 hours until the oxime was consumed.

The resultant mass was cooled to 10° C. and then 250 ml of water was added under vigorous stirring. The resulting mass was transferred to a 5 liter separatory funnel. 500 ml of solvent ether was added to the reaction product and the organics were washed with three 250 ml of water until the aqueous layer was pH neutral. The organic layer was dried over sodium sulfate and the solvent was removed under reduced pressure to provide 115 grams of the crude product.

NMR data 1.35 ppm (t, 3H), 4.2 ppm (q. 2H), 6 ppm (s, 2H), 6.8–7.3 ppm (m, 4H), 8.0 ppm (s, 1H).

The fragrance of this compound was evaluated and was described as heliotropione, cherry-like and sweet.

EXAMPLE 3

Preparation of (1E)-4-(2H-benzo [D] 1,3-dioxolan-5-yl)-1-aza-1-methoxy-3-methylbut-1-ene To a dry 5 liter multi-neck round bottom flask fitted with an air stirrer, nitrogen inlet condenser and an addition funnel, 31 grams of NaH (supplied by Fluka as a 60% dispersion in oil) was added. The flask was maintained at a constant temperature of 20° C. via a water bath. The NaH was washed with three 30 milliliter doses of petroleum ether and the washings were discarded. Tetrahydrofuran (THF) was added to the flask (350 ml), followed by 135 grams of helional oxime in 350 ml of THF over a two hour period while being vigorously stirred. After the addition was complete, 110 grams of methyl iodide in 250 ml of THF was slowly added over two hours. The resulting mixture was stirred at room temperature for 24 hours until the oxime was consumed.

The thick white mass was cooled to 10° C. and then 250 ml of water was added under vigorous stirring. The resulting mass was transferred to a 5 liter separatory funnel. One liter of solvent ether was added to the reaction product and the organics were washed with three 500 ml of water until the aqueous layer was pH neutral. The organic layer was dried over sodium sulfate and the solvent was removed under reduced pressure to provide 105 grams of the crude product.

NMR data 1.1 (d, 3H), 2.4–2.8 ppm (m, 3H), 3.82 ppm (s, 3H), 5.90 ppm (s, 2H), 6.45–7.35 ppm (m, 5H).

The fragrance of this compound was evaluated and was described as floral and green.

EXAMPLE 4

Preparation of 1,3-benzodioxole-5-carboxaldehyde, O-2-propenyloxime

Fifty grams of NaH was added to a dry 5 liter multi-neck, round bottom flask fitted with an air stirrer, nitrogen inlet, condenser, addition funnel and a thermo-well. The flask was maintained at 20° C. through the use of a water bath. The NaH was washed with 3×75 milliliters of petroleum ether and the washings were discarded. Tetrahydrofuran (400 ml) was added to the NaH. Heliotropine oxime (181 grams in 400 ml of tetrahydrofuran) was slowly added to the NaH over a period of 3 hours with vigorous stirring. After the oxime was added, 136 grams of allyl bromide (Aldrich) in 200 ml of THF was slowly added over a period of 2 hours. The mixture was stirred at room temperature for 2 days until the disappearance of the oxime. The thick white mass was cooled to about 10° C. and then 250 ml of water was slowly added under solvent ether to the mass and the organics were washed with 3×250 ml of water until the solvent was removed under reduced pressure.

The oxime ether product appears on the GC at 21.73 minutes. The column was a BPX-5 (25 meter column) operated at a temperature range of 100° C.-3 degrees/minute–200° C.

The crude product was distilled without a column to provide 138 grams of the desired product (92% purity).

The material from the simple distillation was fractionated using a one foot column with steel mesh packing. The following fractions were cut.

Fraction 1=5 grams (boiling range: 95–108° C. at approximately 1.0 mm Hg) 30.1% purity.
Fraction 2=4 grams (boiling range: 111° C. at approximately 1.0 mm Hg) 74.7 purity.
Fraction 3=4 grams (boiling range: 111–114° C. at approximately 1.0 mm Hg).
Fraction 4=4 grams (boiling range: 114–115° C. at approximately 1.0 mm Hg) 95.8% purity.
Fraction 5=4 grams (boiling range: 115° C. at approximately 1.0 mm Hg) 97.52% purity.
Fraction 6=4 grams (boiling range: 115–116° C. at approximately 1.0 mm Hg).
Fraction 7=4 grams (boiling range: 116–117° C. at approximately 1.0 mm Hg) 98.4% purity.
Fraction 8=45 grams (boiling range: 117° C. at approximately 1.0 mm Hg) 99.98% purity.

NMR data 4.65 ppm (2s, 2H), 5.25–5.35 ppm (2d, 2H), 6.0 ppm (s, 2H), 6.05–6.1 ppm(m, 1H), 6.75–7.3 ppm (m, 4H), 8.0 ppm (s, 1H).

The fragrance of this compound was evaluated and was described as floral, fruity, green and sweet.

EXAMPLE 5

Preparation of 1,3-benzodioxole-5-carboxaldehyde, O-(2-methyl-2-propenyl) oxime 55 grams of NaH (Fluka provided as a 60% dispersion in oil) is provided to a dry 5 liter multi-necked round bottom flask fitted with an air stirrer, nitrogen inlet, condenser, addition funnel and thermo-well. The vessel was kept in a water bath whose temperature was maintained at 20° C. The NaH was washed with 3×75 milliliters of petroleum ether and the washings were discarded. Tetrahydrofuran (400 ml) was added to the NaH. Heliotropine oxime (200 grams in 400 ml of tetrahydrofuran) was slowly added to the NaH over a period of 3 hours with vigorous stirring. After the oxime was added, 125 grams of methallyl chloride (Aldrich) in 200 ml of THF was slowly added over a period of 2 hours. The mixture was stirred overnight and the flask was cooled to about 15° C. NaI (Merck, 495 grams) was added over a period of 2 hours and the mixture was stirred at room temperature until the oxime was consumed. The thick white mass was cooled to a temperature of about 10° C. and then 400 ml of water was slowly added under vigorous stirring. The resulting material was transferred to a 5 liter separatory funnel. Solvent ether (1000 ml) was added to the mass and the organic material was washed with 3–500 ml of water until the layer was neutral pH. The organic layer was dried over sodium sulfate and the solvent was removed under reduced pressure to provide 192 grams of the crude material (approximate 77.25% yield).

The oxime ether product appears on the GC at 25.08 minutes. The column was a BPX-5 (25 meter column) operated at a temperature range of 100° C.–3 degrees/minute–200° C.

The product was fractionated using a one foot column with steel mesh packing. Combined front—65 grams (boiling range: 69° C.–140° C. at approximately 1 mm Hg) 67.18% purity. Fraction 4–30 grams (boiling range: 140–142° C. at approximately 1.0 mm Hg) 97.05% purity. Fraction 5–50 grams (boiling range: 142° C. at approximately 1.0 mm Hg) 99.32% purity; undistilled residues 28 grams. NMR data 1.8 ppm (s,3H), 4.55 (s,2H), 5 ppm (2s, 2H), 6 ppm (s, 2H), 6.75–7.2 ppm (m, 4H), 8 ppm (s, 1H).

The fragrance of this compound was evaluated and was described as having heliotropine notes.

EXAMPLE 6

Incorporation of an oxime in a hypothetical fragrance formulation:

| Material | Parts |
| --- | --- |
| Acetyl iso eugenol | 1.0 |
| 1,3-benzodioxole-5-carboxaldehyde, O-(2-methyl-2-propenyl) oxime | 40 |
| Canthoxal | 10 |
| Cinnaminic alcohol (10% in DPG) | 10 |
| Dipropylene glycol | 417 |
| Ethyl vanillin (10% in DPG) | 2 |
| Heliotropine | 50 |
| Vanitrope (10% in DPG) | 50 |
| Veratrald | 120 |

The above formulation is presented to show the level of incorporation of an oxime ether of the present invention in a fragrance composition.

What is claimed is:

1. A method for improving, enhancing or modifying a fragrance through the addition of an olfactory acceptable amount of the compound selected from the group consisting of:

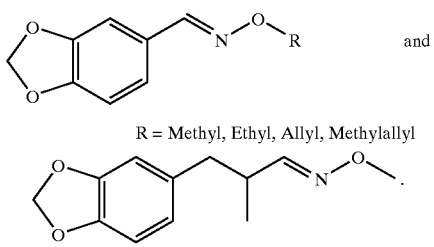

R = Methyl, Ethyl, Allyl, Methylallyl

2. The method of claim 1 wherein the fragrance is incorporated into a product selected from perfumes, colognes, candles, toilet waters, cosmetic products, personal care products, fabric care products, cleaning products and air fresheners.

3. The method of claim 2 wherein the cleaning product is selected from the group consisting of soaps, detergents, dishwashing compositions, scrubbing compounds and window cleaners.

4. The method of claim 2 wherein the product is a personal care product.

5. The method of claim 1 wherein the level is from about 0.005 to about 10 weight percent.

6. The method of claim 1 wherein the level is from about 0.1 to about 8 weight percent.

7. The method of claim 1 wherein the level is from about 0.5 to about 5 weight percent.

8. The method of claim 1 wherein the compound is selected from the group consisting of 1,3-benzodioxole-5-carboxaldehye, O-methyloxamine; 1,3-benzodioxole-5-carboxaldehye, O-ethyloxamine; 1,3-benzodioxole-5-carboxaldehye, O-allyloxamine; and 1,3-benzodioxole-5-carboxaldehye, O-methallyloxamine.

9. The method of claim 1 wherein the compound is helional oxime methyl ether.

10. The method of claim 1 wherein the compound contains an allyl group.

11. The method of claim 8 wherein the fragrance is incorporated into a product selected from perfumes, colognes, candles, toilet waters, cosmetic products, personal care products, fabric care products, cleaning products and air fresheners.

12. The method of claim 9 wherein the fragrance is incorporated into a product selected from perfumes, colognes, candles, toilet waters, cosmetic products, personal care products, fabric care products, cleaning products and air fresheners.

13. The method of claim 10 wherein the fragrance is incorporated into a product selected from perfumes, colognes, candles, toilet waters, cosmetic products, personal care products, fabric care products, cleaning products and air fresheners.

14. The compound of the formula:

R=H and Me

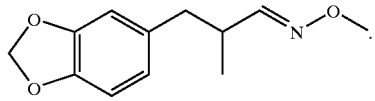

15. A fragrance product made by the method of claim 1.

16. A fragrance formulation containing an olafactory effective amount of compound of claim 1.

* * * * *